United States Patent
Smothers

(10) Patent No.: US 6,949,262 B1
(45) Date of Patent: Sep. 27, 2005

(54) SKIN AND MUCOSAL TREATMENT FORMULATION

(75) Inventor: Don L. Smothers, Dallas, TX (US)

(73) Assignee: LouSal Enterprises, Inc., Aledo, TX (US)

( * ) Notice: Subject to any disclaimer, the term of this patent is extended or adjusted under 35 U.S.C. 154(b) by 0 days.

(21) Appl. No.: 10/445,794

(22) Filed: May 27, 2003

(51) Int. Cl.$^7$ .................. A61K 31/74; A61K 35/78
(52) U.S. Cl. .................. 424/744; 424/78.03; 514/783
(58) Field of Search .................. 424/744, 78.03; 514/783

(56) References Cited

U.S. PATENT DOCUMENTS

| | | | |
|---|---|---|---|
| 4,781,923 A | | 11/1988 | Pellico |
| 4,959,214 A | * | 9/1990 | McAnalley |
| 5,000,936 A | * | 3/1991 | Chibret .................. 424/43 |
| 5,604,200 A | * | 2/1997 | Taylor-McCord |
| 5,760,079 A | * | 6/1998 | Shaffer et al. |
| 6,391,330 B1 | | 5/2002 | Ross |

FOREIGN PATENT DOCUMENTS

| | | |
|---|---|---|
| EP | 001210946 A1 * | 11/2001 |
| WO | WO 03/030793 | 4/2003 |

* cited by examiner

*Primary Examiner*—Michele Flood
(74) *Attorney, Agent, or Firm*—Jacqueline S. Larson

(57) ABSTRACT

A treatment composition for use in providing relief of dryness of the nasal tissues and other dry skin, and particularly to providing such relief without the use of petroleum products.

11 Claims, No Drawings

SKIN AND MUCOSAL TREATMENT FORMULATION

FIELD OF THE INVENTION

The present invention is directed to a skin and mucosal treatment composition to aid in the relief of skin dryness, including within the nasal cavity.

BACKGROUND OF THE INVENTION

During times of sickness or when the local environment is low in humidity, the tissues of the inside of the nose can become dried out. This nasal dryness may cause discomfort, soreness, congested breathing, and even bleeding and the associated possibility of nasal infections.

One particular problem area is skin dryness that causes cracking and bleeding tissue when associated with oxygen administration by means of plastic nasal cannula over an extended period of time, or chafing and irritation resulting from unprotected skin subjected to continuous air flow when continuous positive airway pressure (CPAP) therapy is used for treatment of sleep disorders, such as apnea.

While there are various moisturizers and gels available for treatment of nasal cavity and topical skin dryness, they generally include petroleum in their formulations. However, petroleum cannot be used in areas exposed to high oxygen content. Thus, these products cannot be used by persons on oxygen therapy or CPAP therapy.

SUMMARY OF THE INVENTION

The present invention is directed to providing relief of dryness of the nasal tissues and other dry skin, and particularly to providing such relief over an extended period of time and without the use of petroleum products.

More particularly, the present invention is directed to a skin and mucosal treatment composition that is applied to mucosa (such as nasal tissue) or to the skin (such as facial areas exposed to an oxygen mask) and remains in place for a substantial period of time, and which can release moisture to the nasal tissues or treated skin and also forms a barrier on the exposed area to protect it from the drying and chafing activity caused by dry climates, continuous oxygen flow, or oxygen-delivery equipment. By doing so, the user is more comfortable and the nasal tissues and other exposed skin are healthier, without reliance on petroleum products.

The present invention provides a skin and mucosal composition comprising: aloe, dimethicone, allantoin, and water in a carrier base such as an oil, a cream, or a gel.

DETAILED DESCRIPTION OF THE INVENTION

As used herein and in the accompanying claims, the terms "a" and "an" mean "one or more", unless otherwise indicated.

The components of the petroleum-free skin and mucosal treatment composition of the present invention are chosen to be safe for use on the nasal tissues and to be non-irritating.

Useful formulations of the skin and mucosal composition comprise aloe in an amount ranging from about 35 wt % to about 80 wt %, dimethicone in an amount ranging from about 1 wt % to about 3 wt %, allantoin in an amount ranging from about 0.5 wt % to about 3 wt %, and water in an amount ranging from about 20 wt % to about 40 wt %. One presently preferred formulation of the invention comprises about 50 wt % aloe vera, about 2 wt % dimethicone, about 0.6 wt % allantoin, about 35 wt % water, and about 12.4 wt % other ingredients.

Other ingredients or components may be included in the skin and mucosal composition of the invention. Such other components may be selected from, but are not limited to: humectants, preservatives, emollients, buffers, coloring agents, fragrances, solubilizing agents, stabilizing agents, gel-forming agents, oils, antibiotics, herbal materials, and vitamins. Each of these ingredients can be present in any amount that does not substantially interfere with the skin-protecting and skin-moisturizing functions of the treatment composition.

The hydrating skin and mucosal compositions of the present invention are effective at a viscosity preferably ranging from between about 5,000 centipoise to about 300,000 centipoise at room temperature (RT), or about 25° C. Preferably, the viscosity of the composition of the invention is between about 20,000 and about 100,000 centipoise at RT, and more preferably between about 25,000 and 60,000 centipoise.

To treat dry skin or mucosa, the skin and mucosal treatment composition of the invention is administered to the area(s) of the skin or mucosa that exhibit discomfort, soreness, cracking, bleeding, chafing, irritation, or other symptoms of dryness. The treatment composition is applied in an amount and at time intervals as necessary to provide relief from such symptoms. For example, for oxygen users, the composition can be applied at any time during oxygen therapy in sufficient amounts to both the internal and external membranes of the nasal passage, as well as over the ear to reduce friction created by cannula rubbing. CPAP users can apply the treatment composition to the facial area where the oxygen mask meets and covers the skin before beginning therapy. The treatment composition of the invention will not leave a sticky residue on the skin.

The following example further illustrates the invention. However, the invention is not limited thereto, and it will be apparent to those of ordinary skill in the art from the teachings herein that equivalent modifications thereof may be made without departing from the spirit and scope of this invention.

EXAMPLE 1

A skin and mucosal composition was prepared according to the formula shown in Table I.

TABLE I

| Ingredient | Weight % |
| --- | --- |
| Aloe Vera | 50.000 |
| Water | 34.886 |
| Glycerine 99.5% USP | 4.000 |
| Rice Bran Oil | 2.000 |
| Emu Oil | 2.000 |
| Dimethicone | 2.000 |
| DEA oleth-3 phosphate[1] | 2.000 |
| Carbopol 940 | 1.000 |
| Triethanolamine 99% | 0.600 |
| Allantoin | 0.600 |
| Undebenzophene-C | 0.500 |
| Sodium hydroxymethylglycinate[2] | 0.200 |
| Tocopherol Acetate | 0.100 |
| d-L Panthenol | 0.100 |
| Fragrance - Baby Powder | 0.010 |
| Vitamin A Acetate | 0.004 |

[1]Crodofos ® N3 Neutral, Croda, Parsippany, NJ
[2]Suttocide-A ®, Van Wagoner and Associates, Highland Village, TX

PHASE-1

The water and glycerin were mixed together, after which Carbopol was added and dispersed into the mixture with high shear until completely smooth with no lumps. The mixture was then heated to 65° C.

PHASE-2

The emu oil, undebenzophene, DEA oleth-3 phosphate, vitamin A acetate, dimethicone and rice bran oil were mixed together and heated to 65° C.

PHASE-3

The aloe vera, Suttocide A, allantoin, panthenol and tocopherol acetate were added together and agitated until completely dissolved.

When the heated phases reached the specified temperatures, PHASE 2 was added to PHASE 1 until the emulsion was smooth and free of lumps. PHASE 3 was then added to the emulsion with high shear until homogeneous. Cooling of the resulting mixture was begun, with continued regular agitation, and triethanolamine was added. When the batch reaches 30° C., the fragrance was added, with continued agitation, and the pH was adjusted to 5.6±0.3. The final product had the following specifications:

| | |
|---|---|
| Color | white to off-white |
| Odor | light fragrance |
| Appearance | soft cream |
| Viscosity | 32,000–52,000 cps |
| Specific Gravity | 0.995–1.005 |
| Microbiological Profile: | |
| Total Count | 10 cfu/mL max. |
| Pathogenic Bacteria | none |
| Mold or yeast | none |

What is claimed is:

1. A skin and mucosal treatment composition comprising of the total amount of the composition:
    Aloe vera in an amount ranging from about 35 weight % to about 80 weight %,
    dimethicone in an amount ranging from about 1.5 weight % to about 3 weight %,
    allantoin in an amount ranging from about 0.5 weight % to about 3 weight %, and
    water in an amount ranging from about 20 weight % to about 40 weight %.

2. A composition according to claim 1, which is free of petroleum products.

3. A composition according to claim 2, which further comprises one or more additional components selected from the group consisting of humectants, preservatives, emollients, buffers, coloring agents, fragrances, solubilizing agents, stabilizing agents, gel-forming agents, oils, antibiotics, herbal materials, and vitamins.

4. A composition according to claim 2, which comprises of the total amount of the composition about 50 weight % Aloe vera, about 2 weight % dimethicone, about 0.6 weight % allantoin, about 35 weight % water, and about 12.4 weight % other ingredients.

5. A composition according to claim 4, wherein the other ingredients are selected from the group consisting of humectants, preservatives, emollients, buffers, coloring agents, fragrances, solubilizing agents, stabilizing agents, gel-forming agents, oils, antibiotics, herbal materials, and vitamins, and mixtures thereof.

6. A composition according to claim 2 comprising Aloe vera, dimethicone, allantoin, water, glycerin, rice bran oil, emu oil, diethanolamine salt of oleth-3 phosphate, Carbopol®(high molecular weight acrylic acid-polyalkenyl polyether polymers), triethanolamine, undebenzophene, sodium hydroxymethylglycinate, tocopherol acetate, panthenol, vitamin A, and fragrance.

7. A skin and mucosal treatment composition comprising of the total amount of the composition:
    Aloe vera in an amount ranging from about 35 weight % to about 80 weight %,
    dimethicone in an amount ranging from about 1 weight % to about 3 weight %,
    allantoin in an amount ranging from about 0.5 weight % to about 3 weight %, and
    water in an amount ranging from about 20 weight % to about 40 weight %;
    said treatment composition being free of petroleum products.

8. A composition according to claim 7, which further comprises one or more additional components selected from the group consisting of humectants, preservatives, emollients, buffers, coloring agents, fragrances, solubilizing agents, stabilizing agents, gel-forming agents, oils, antibiotics, herbal materials, and vitamins.

9. A composition according to claim 7, which comprises of the total amount of the composition about 50 weight % Aloe vera, about 2 weight % dimethicone, about 0.6 weight % allantoin, about 35 weight % water, and about 12.4 wt weight other ingredients.

10. A composition according to claim 9, wherein the other ingredients are selected from the group consisting of humectants, preservatives, emollients, buffers, coloring agents, fragrances, solubilizing agents, stabilizing agents, gel-forming agents, oils, antibiotics, herbal materials, and vitamins, and mixtures thereof.

11. A composition according to claim 7 comprising Aloe vera, dimethicone, allantoin, water, glycerin, rice bran oil, emu oil, diethanolamine salt of oleth-3 phosphate, Carbopol®(high molecular weight acrylic acid-polyalkenyl polyether polymers), triethanolamine, undebenzophene, sodium hydroxymethylglycinate, tocopherol acetate, panthenol, vitamin A, and fragrance.

* * * * *